United States Patent
Yoshioka et al.

(10) Patent No.: US 7,531,794 B2
(45) Date of Patent: May 12, 2009

(54) METHOD AND APPARATUS FOR PREPARING SPECIMEN

(75) Inventors: Tadanori Yoshioka, Kouchi (JP); Kiyoshi Kawatsu, Tokyo (JP); Hirofumi Miyao, Tokyo (JP)

(73) Assignee: Jeol Ltd., Tokyo (JP)

( * ) Notice: Subject to any disclaimer, the term of this patent is extended or adjusted under 35 U.S.C. 154(b) by 484 days.

(21) Appl. No.: 11/408,795

(22) Filed: Apr. 21, 2006

(65) Prior Publication Data

US 2006/0255295 A1    Nov. 16, 2006

(30) Foreign Application Priority Data

Apr. 21, 2005    (JP) .............................. 2005-123560

(51) Int. Cl.
    *G01N 31/00*    (2006.01)
(52) U.S. Cl. ....................... 250/304; 250/306; 250/307
(58) Field of Classification Search ................. 250/304, 250/306–443.1, 492.1–492.3
    See application file for complete search history.

(56) References Cited

U.S. PATENT DOCUMENTS 5,656,811 A * 8/1997 Itoh et al. .................... 250/309
5,907,157 A   5/1999 Yoshioka et al.

FOREIGN PATENT DOCUMENTS

JP    3263920    8/1997
JP    2004-283802    10/2004

* cited by examiner

*Primary Examiner*—David A Vanore
*Assistant Examiner*—Andrew Smyth
(74) *Attorney, Agent, or Firm*—The Webb Law Firm

(57) ABSTRACT

Preparing a thin-film specimen adapted for TEM (transmission electron microscopy) observation. A high-brightness pixel extraction unit extracts high-brightness pixels which form a specimen image taken by an imaging unit. The intensities becoming greater than a given threshold value as the specimen is thinned. A decision unit makes a decision as to whether the high-brightness pixels extracted by the high-brightness pixel extraction unit form a continuous sequence of pixels whose number is in excess of a given number on the specimen image. If the decision is affirmative, the decision unit sends a signal to an ion gun control unit to stop the ion-beam irradiation of the specimen.

9 Claims, 10 Drawing Sheets

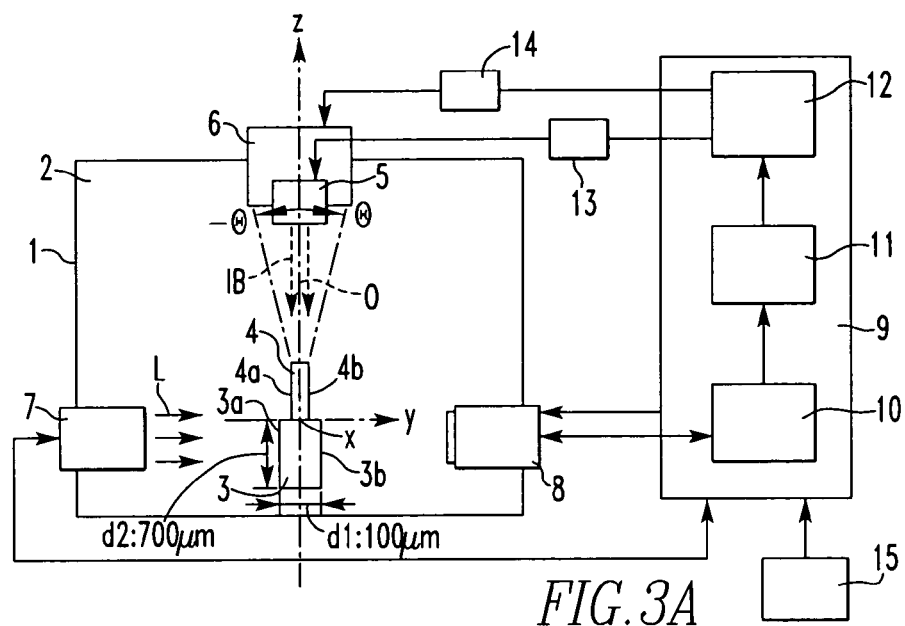
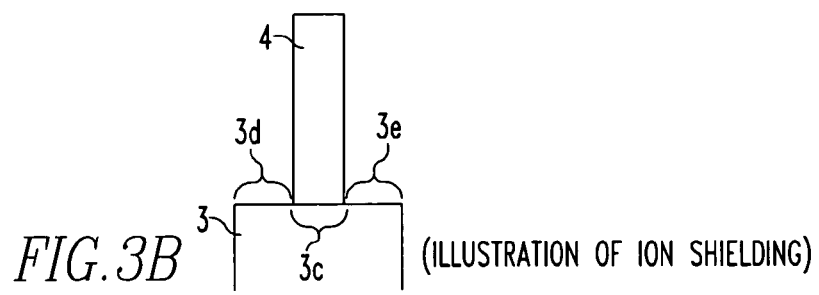
FIG.3B (ILLUSTRATION OF ION SHIELDING)
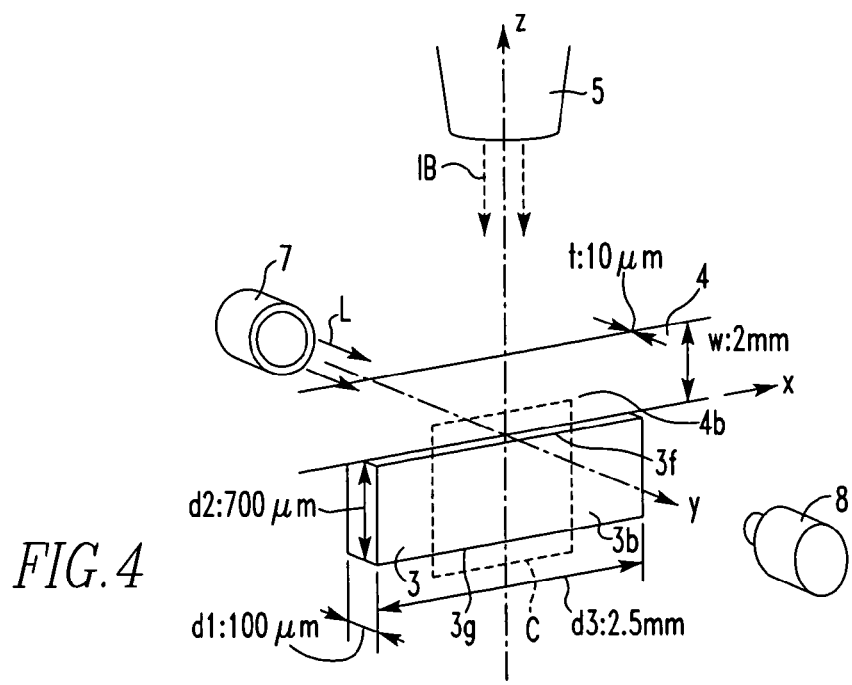
FIG.4

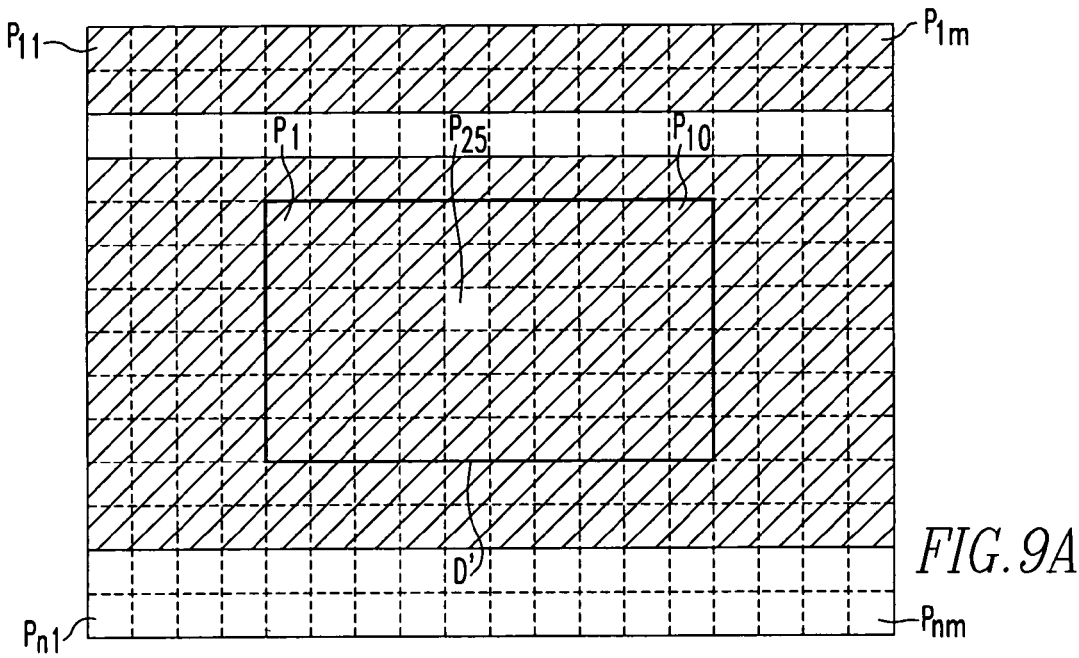
FIG. 9A
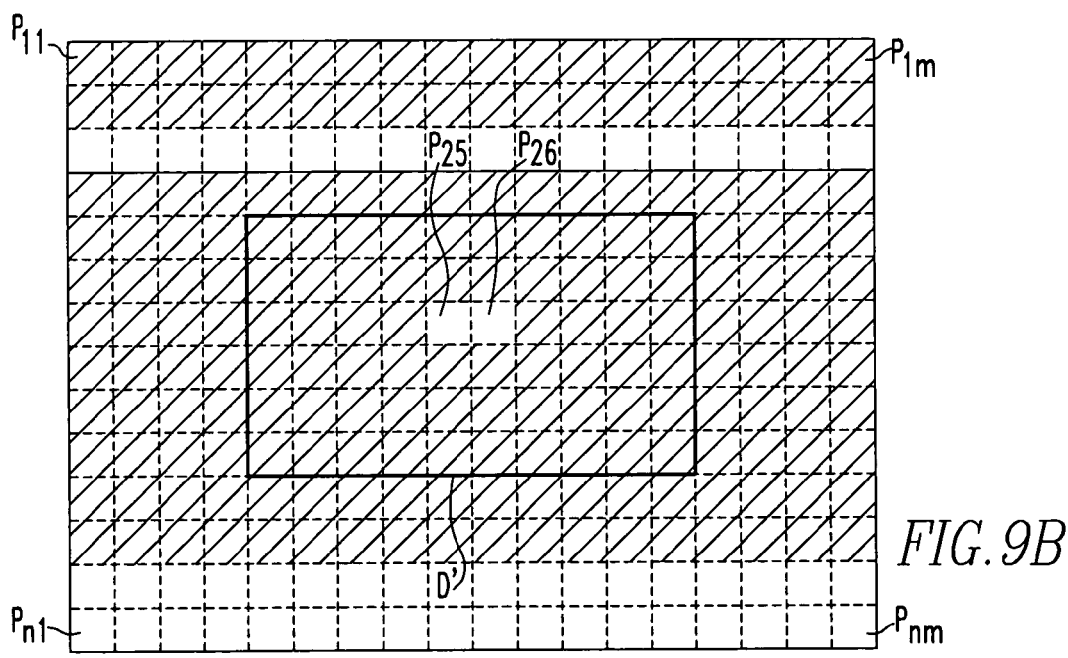
FIG. 9B
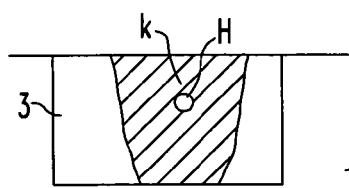
FIG. 9C

METHOD AND APPARATUS FOR PREPARING SPECIMEN

BACKGROUND OF THE INVENTION

1. Field of the Invention

The present invention relates to a method and apparatus for preparing a specimen observed with a transmission electron microscope or other similar instrument.

2. Description of Related Art

As a method of preparing a thin-film specimen observed with a transmission electron microscope (TEM), a method described, for example, in Japanese Patent No. 3,263,920, has been heretofore known. In this known method, a shielding material is placed over a specimen. An ion beam is directed from above the shielding material at both shielding material and specimen.

The specimen portions not shielded with the shielding material are ion-etched. At this time, the shielding material is moved in two steps over the specimen and etched to finish the thin-film specimen.

The above-cited Japanese patent has been filed by the present applicant. Last year, the present applicant filed a patent application for a novel specimen preparation method for obtaining thin-film specimens with higher reliability (Japanese Patent Application No. 2004-283802). In this method, as shown in FIG. 1A, a belt-like shielding material is placed over a specimen so as to stand almost uprightly. Ion beams are directed at the shielding material and specimen from leftward and rightward above the shielding material. The specimen is ion-etched to form a through-hole h around the center of the specimen. A peripheral portion A around the through-hole h is a thin film. The thin film A has a thickness adapted for TEM observation. FIG. 1B is a view of the specimen of FIG. 1A, taken from a side surface B.

In the method shown in FIG. 1A, when the through-hole h is formed in the specimen, i.e., when the thin film A having a thickness adapted for TEM observation is completed, the ion-beam irradiation of the specimen must be stopped, for the following reason. If the ion beam is still directed at the specimen even after the through-hole h has been formed in the specimen, the peripheral portion A is etched further and rounded as shown in FIG. 2. As a result, the thickness of the peripheral portion A increases to such a level that TEM observation can no longer be performed.

In this way, in the method shown in FIG. 1A, it is quite important to stop the ion-beam irradiation immediately after formation of the through-hole h in the specimen. We have tried to develop apparatus for automatically stopping the ion-beam irradiation. During the developmental stage, various well-known techniques were attempted to stop the ion-beam irradiation at good timing with unsuccessful results. For example, in one attempt to automatically stop the ion-beam irradiation, light was directed at a specimen, and light transmitted through the specimen was detected. When the intensity of the transmitted light exceeded a threshold value, the irradiation was stopped. However, appropriate timing of stoppage was not achieved. It was not possible to prepare thin-film specimens adapted for TEM observation reliably.

SUMMARY OF THE INVENTION

It is an object of the present invention to provide a method and apparatus capable of reliably preparing a good thin-film specimen adapted for TEM observation.

A specimen fabrication method according to one aspect of the present invention which achieves the above-described object is used to thin a specimen by irradiating at least one of left and right side surfaces of the specimen with an ion beam so as to ion-etch the specimen. The irradiation of the ion beam is stopped or conditions under which the specimen is irradiated with the ion beam are varied by the following process steps (a)-(d).

(a) The specimen is irradiated with the ion beam. Also, any one of the left and right side surfaces of the specimen is illuminated with light. The other side surface of the specimen is imaged by an imaging means.

(b) Each sensed specimen image is made up of pixels. Each pixel gives a level of brightness. As the specimen is thinned, those pixels which produce brightness levels in excess of a given threshold value are extracted as high-brightness pixels.

(c) A decision is made as to whether the extracted high-brightness pixels form a continuous sequence of more than a given number of pixels on the specimen image.

(d) If the decision at the step (c) is affirmative (YES), the ion-beam irradiation of the specimen is stopped or the irradiation conditions are varied.

Accordingly, the present invention can provide a method and apparatus capable of reliably preparing good thin-film specimens adapted for TEM observation.

Other objects and features of the invention will appear in the course of the description thereof, which follows.

BRIEF DESCRIPTION OF THE DRAWINGS

FIG. 3A is a block diagram of a specimen preparation apparatus according to one embodiment of the present invention;

FIG. 3B is an illustration of ion shielding;

FIG. 4 is a perspective view illustrating the apparatus shown in FIG. 3A;

FIGS. 9A, 9B, and 9C illustrate the operation of the apparatus shown in FIG. 3A;

DESCRIPTION OF THE PREFERRED EMBODIMENTS

Figure 1A:
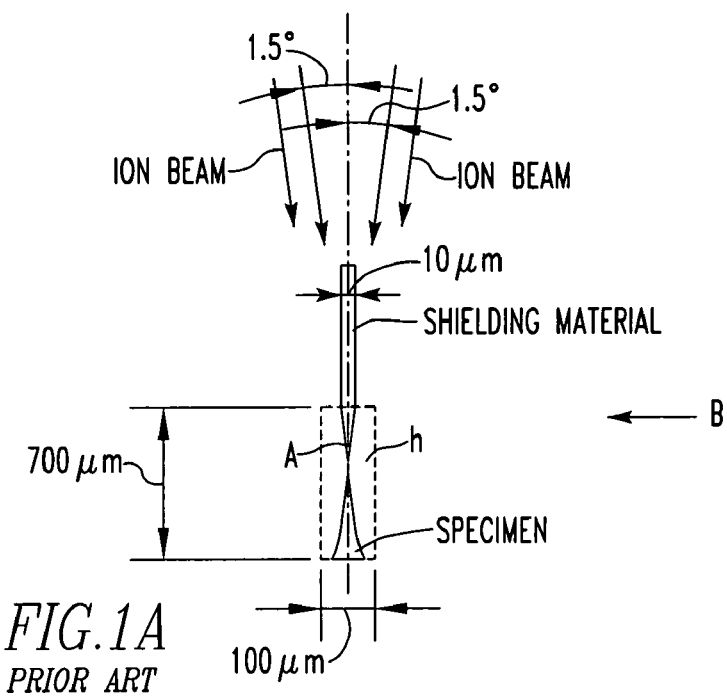
FIGS. 1A and 1B illustrate the manner in which a specimen is prepared by a known method.
Figure 1B:
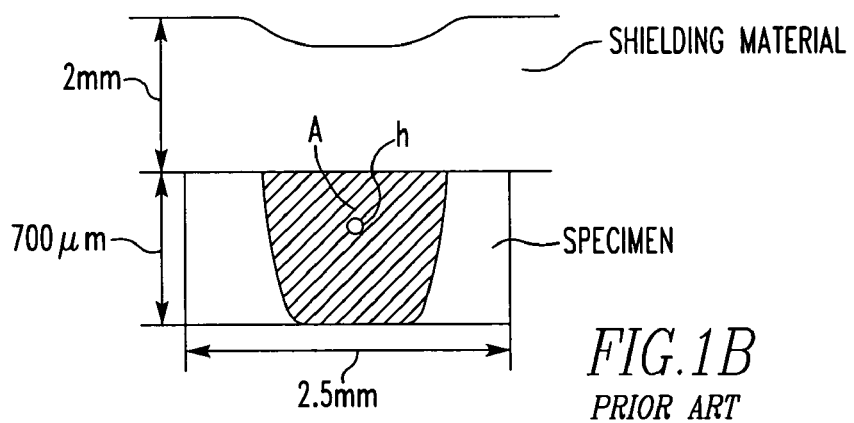
Figure 2:
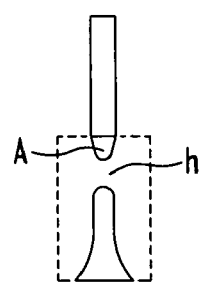
FIG. 2 is a view illustrating the problem with the known method illustrated in FIG. 1.

Some embodiments of the present invention are hereinafter described with reference to the accompanying drawings.

Referring to FIGS. 3A and 3B, there is shown a specimen preparation apparatus according to one embodiment of the present invention. The configuration of the apparatus is first described.

This apparatus has a vacuum chamber 1 including a specimen chamber 2. The inside of the specimen chamber 2 is evacuated by a pumping system (not shown). A specimen 3 and a shielding material 4 are placed in the specimen chamber 2. The specimen 3 and shielding material 4 are set on their respective holders (not shown).

The specimen 3 has a thickness $d_1$ of about 100 μm, a vertical dimension $d_2$ of about 700 μm, and a lateral dimension $d_3$ of about 2.5 mm as given in the perspective view of FIG. 4, which depicts the specimen 3 disposed in the specimen chamber 2. Meanwhile, the belt-like (or ribbon-like or tape-like) shielding material 4 has a thickness t of about 10 μm and a width w of about 2 mm as given in FIG. 4. As shown in FIGS. 3A and 4, the shielding material 4 is placed to stand uprightly over the specimen 3. The shielding material 4 is located on the z-axis and stretched in the x-axis direction.

The gap between the shielding material 4 and the top surface of the specimen 3 is only approximately 10 to 30 μm. Since the shielding material 4 is placed closely over the specimen 3 in this way, an unirradiated surface portion 3c and irradiated surface portions 3d and 3e are formed on the specimen 3 as shown in the insert of FIG. 3B, which illustrates shielding from ions. The irradiated portions 3d and 3e are located on the opposite sides of the unirradiated portion 3c that is covered with the shielding material 4. Therefore, the unirradiated surface portion 3c is not irradiated with the ion beam $I_B$ from an ion gun 5. The shielding material 4 is made of an amorphous metal such as nickel-phosphorus including more than 10% phosphorus.

The ion gun 5 is held to an ion gun-tilting mechanism 6, which, in turn, is mounted to a top portion of the vacuum chamber 1 as shown in FIG. 3A. In the state of FIG. 3A, the optical axis O of the gun 5 is coincident with the z-axis. The tilting mechanism 6 is used to tilt the ion gun 5 left and right at an angle of θ about the x-axis passing over the specimen 3. That is, the tilting mechanism tilts the gun 5 about the z-axis at an angle of θ in the −y-direction and y-direction. A gas ion gun is used as the ion gun 5. For example, the used gas ion gun releases Ar ions by ionizing Ar gas by electric discharging.

A light source 7 that is a light illumination source is mounted to the left side surface of the vacuum chamber 1. The light source 7 is disposed opposite to the left side surface 3a of the specimen 3 and used to illuminate the left side surface 3a with light L. When the light source 7 is not in operation, the specimen chamber 2 is dark.

An imaging device 8, such as a CCD, camera is mounted to the right side surface of the vacuum chamber 1. The imaging device 8 is disposed opposite to the right side surface 3b of the specimen 3. The imaging device 8 is located opposite to the light source 7 with the specimen 3 therebetween. The imaging device 8 is used to image the right side surface 3b of the specimen 3. For example, the imaging device 8 has an imaging area C surrounded by the dotted line in FIG. 4. A portion of the specimen 3 defined from its upper end 3f to its lower end 3g is contained within the imaging area C. The lower end of the shielding material 4 is also contained within the imaging area C.

Referring still to FIG. 3A, a central control unit (CCU) 9 incorporates a high-brightness pixel extraction means 10, a decision means 11, and an ion gun control means 12. The CCU 9 is electrically connected with all of the light source 7, imaging device 8, a voltage source 13 for the ion gun 5, a driver source 14 for the ion gun-tilting mechanism 6, and an input means 15 including a keyboard and a computer mouse. The configuration of the apparatus shown in FIG. 3A has been described so far. The operation is next described.

The operator first enters a "specimen type" from the input means 15 in FIG. 3A. The specimen 3 set currently has been extracted from a bulk specimen. Therefore, in this case, "bulk specimen" is entered. When this input is made, plural specimen types are displayed on the display screen of a CRT connected with the CCU 9. The operator selects the "bulk specimen" from the displayed specimen types by mouse clicking. If the "bulk specimen" is entered in this way, the CCU 9 sets the operation mode of the high-brightness pixel extraction means 10, decision means 11, and gun control means 12 to a "through-hole formation mode" corresponding to the "bulk specimen". That is, in this mode, a through-hole is formed around the center of the specimen 3.

If the operator enters "start of etching" from the input means 15, the gun control means 12 of the CCU 9 operates in the "through-hole formation mode". That is, the gun control means 12 sends a tilt signal $θ_1$ to the driver source 14 to tilt the ion gun 5 to the left (−y-direction) at an angle of $θ_1$ (e.g., 1.5°). In response to the tilt signal $θ_1$, the driver source 14 tilts the gun-tilting mechanism 6. As a result, the ion gun 5 tilts to the left by 1.5° with respect to the z-axis. The value (1.5°) of the tilt signal $θ_1$ has been previously entered and set by the operator from the input means 15.

If the "start of etching" is entered, the gun control means 12 of the CCU 9 sends a signal to the voltage source 13 to release the ion beam $I_B$ from the ion gun 5. The voltage source 13 applies a given voltage between the electrodes of the ion gun 5 to release the ion beam $I_B$. As a result, the ion beam $I_B$ is released from the ion gun 5 tilted at an angle of $θ_1$ (1.5°) to the left with respect to the z-axis.

Figure 5A:
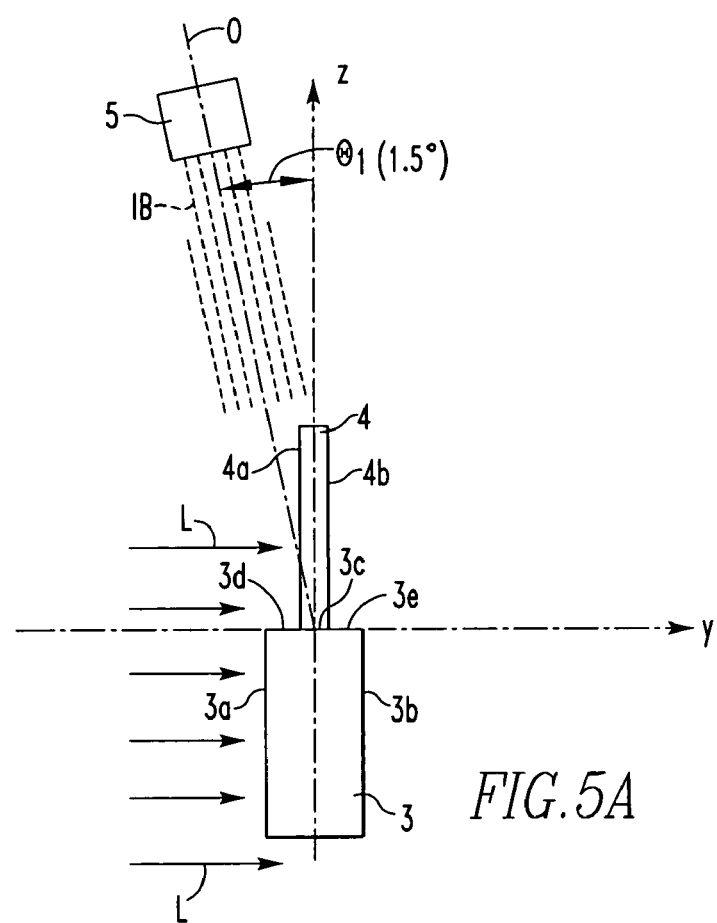
FIGS. 5A and 5B illustrate the operation of the apparatus shown in FIG. 3A.

When the "start of etching" is entered, the CCU 9 turns on the power supply of the light source 7. Consequently, light L is emitted from the light source 7 and hits the left side surface 3a of the specimen 3 and the left side surface 4a of the shielding material 4 as shown in FIG. 5A. As also shown in FIG. 5A, the ion beam $I_B$ emitted from the ion gun 5 and tilted at an angle of $θ_1$ (1.5°) to the left with respect to the z-axis hits the shielding material 4 and specimen 3 obliquely from leftward above the shielding material 4. The ion-beam irradiation is performed for a given time, e.g., 5 minutes.

When the "start of etching" is entered, the CCU 9 sends a signal to the imaging device 8 to operate it. The imaging device 8 then starts to continuously image the surface of the specimen that faces away from the illuminated surface, i.e., the right side surface 3b of the specimen 3. The specimen image (image contained in the area C of FIG. 4) taken by the imaging device 8 is sent to the high-brightness pixel extraction means 10.

Figure 6A:
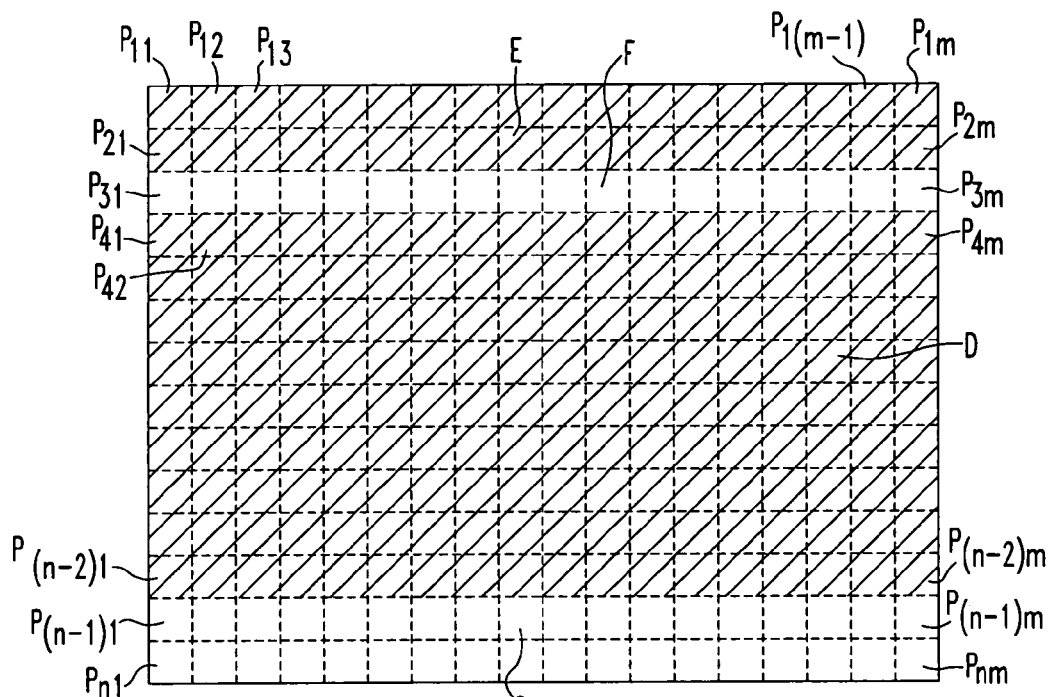
FIGS. 6A, 6B, and 6C illustrate the operation of the apparatus shown in FIG. 3A.

The high-brightness pixel extraction means 10 accepts the specimen images taken by the imaging device 8 at given intervals of time (e.g., at intervals of two seconds). First, the extraction means 10 accepts the specimen image first taken, i.e., a specimen image $I_1$ at the beginning of etching. FIG. 6A shows the accepted specimen image $I_1$. The dotted line indicates the boundary between the pixels. In FIG. 6A, an image D represents the right side surface 3b of the specimen 3. The image D is made up of pixels $p_{41}, p_{42}, \ldots, p_{4m}, p_{(n-2)1}, \ldots, p_{(n-2)m}$. The specimen 3 does not transmit the light L from the light source 7. The right side surface 3b of the specimen 3 is not irradiated with the light. Therefore, the image D is totally dark at the beginning of etching at which a through-hole is not yet formed in the specimen 3.

In FIG. 6A, an image E represents the lower end (right side surface 4b) of the shielding material 4. The image E is made up of pixels $p_{11}, p_{12}, \ldots, p_{1m}, p_{21}, \ldots, p_{2m}$. The image E is totally dark in the same way as the image D.

Furthermore, in FIG. 6A, an image F represents the light L passed through the gap between the shielding material 4 and the specimen 3. The image F is made up of pixels $p_{31}, \ldots, p_{3m}$. The image F is bright in conformity with the brightness of the light L.

In addition, in FIG. 6A, an image G represents the light L passed under the specimen 3. The image G is made up of pixels $p_{(n-1)1}, \ldots, p_{(n-1)m}, \ldots, p_{nm}$. The image G is bright in conformity with the brightness of the light L, in the same way as the image F.

Figure 6B:
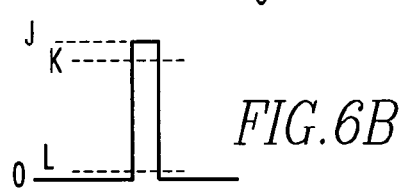

(1) The high-brightness pixel extraction means 10 compares the signal intensities from the pixels ($p_{11}$ to $p_{nm}$) making up the accepted specimen image $I_1$ produced at the beginning of etching with a threshold value K, and extracts pixels having intensities greater than the threshold value K. The threshold value K has been previously set by the operator from the input means 15 such that pixels (pixels $p_{31}, \ldots, p_{3m}$ and $p_{(n-1)1}, \ldots, p_{(n-1)m}, \ldots, p_{nm}$ at the present time) representing the light L are extracted. That is, as shown in FIG. 6B, the threshold value K is set to a value slightly lower than the intensity J of the pixels representing the light L. At the present time, the intensities of pixels $p_{41}, p_{42}, \ldots, p_{4m}, \ldots, p_{(n-2)1}, \ldots, p_{(n-2)m}$ making up the image D of the right side surface of the specimen and the intensities of pixels $p_{11}, p_{12}, \ldots, p_{1m}, p_{21}, \ldots, p_{2m}$ making up the image E of the shielding material are the intensity L in FIG. 6B. The intensity L is almost zero.

(2) Since the threshold value K is set as described above, the high-brightness pixel extraction means 10 extracts pixels $p_{31}, \ldots, p_{3m}$ and $p_{(n-1)m}, \ldots, p_{(n-1)m}, \ldots, p_{nm}$ representing the light L. The extraction means 10 extracts the pixels representing the light L, thus identifying pixels corresponding to the upper end (3f) and lower end (3g), respectively, of the specimen 3. That is, the extraction means 10 identifies pixels $p_{41}, p_{42}, \ldots, p_{4m}$ as pixels corresponding to the upper end (3f) of the specimen, based on the extracted pixels $p_{31}, \ldots, p_{3m}$. Similarly, the extraction means 10 identifies pixels $p_{(n-2)1}, \ldots, p_{(n-2)m}$ as pixels corresponding to the lower end (3g) of the specimen, based on the extracted pixels $p_{(n-1)1}, \ldots, p_{(n-1)m}$.

(3) The high-brightness pixel extraction means 10 recognizes the pixel region of the image D of the right side surface of the specimen by identifying the pixels corresponding to the upper end (3f) of the specimen and the lower end (3g) of the specimen, respectively, in this way. In this case, the extraction means 10 recognizes that the image D of the right side surface of the specimen is made up of pixels $p_{41}, p_{42}, \ldots, p_{4m}, \ldots, p_{(n-2)1}, \ldots, p_{(n-2)m}$.

Figure 6C:
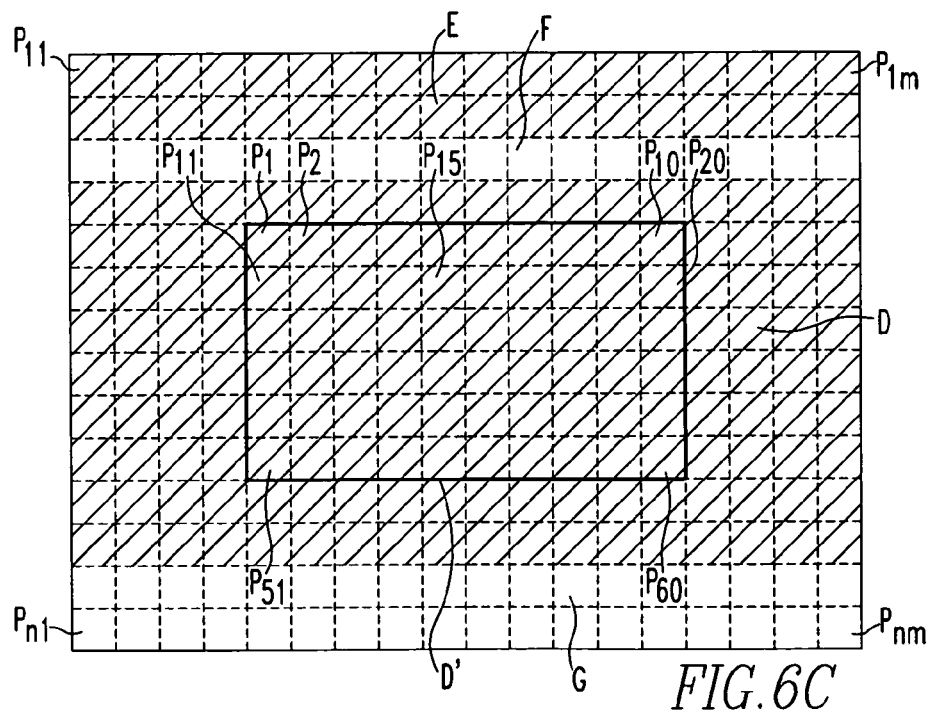

(4) After recognizing the pixel region of the image D of the right side surface of the specimen in this way, the high-brightness pixel extraction means 10 sets a decision region D' within the pixel region. The extraction means 10 sets the decision region D', for example, as shown in FIG. 6C. The decision region D' includes pixels $p_1$ to $p_{60}$ and is set in a central portion of the image D such that formation of a through-hole in the central portion of the specimen can be detected.

(5) The high-brightness pixel extraction means 10 refers to the results of the extraction performed in step (1) above and makes a decision as to whether the pixels $p_1$ to $p_{60}$ within the decision region D' contain high-density pixels P having intensities greater than the threshold value K. If the ion etching progresses and a through-hole is formed in the specimen 3, the light L passes through the through-hole and is detected by the imaging device 8. Therefore, any ones of the pixels $p_1$ to $p_{60}$ within the decision region D' come to have intensities greater than the threshold value K. However, at the beginning of etching, no through-hole is formed in the specimen 3 and so no high-brightness pixels P are present within the decision region D'. Only when such high-brightness pixels P exist, the extraction means 10 sends the information to the decision means 11. Therefore, the decision means 10 produces no output to the decision means 11 in this case.

The processing (process steps (1)-(5)) performed by the high-brightness pixel extraction means 10 regarding the specimen image $I_1$ has been described so far. When a period of 2 seconds elapses since the acceptance of the specimen image $I_1$, the extraction means 10 accepts the specimen image $I_2$ taken by the imaging device 8. Then, the extraction means 10 performs the process steps (1)-(5) regarding the specimen image 12. At this point, no through-hole is yet formed in the specimen 3. In the process step (5), the high-brightness pixels P are not extracted. Therefore, the extraction means 10 outputs no signal to the decision means 11.

Subsequently, the extraction means 10 accepts specimen images $I_3, I_4, \ldots$ at intervals of 2 seconds and performs the process steps (1)-(5) regarding each specimen image. In practice, a through-hole is formed in the specimen 3 after a period of more than 1 hour has elapsed since the start of ion etching. Consequently, the extraction means 10 produces no output to the decision means 11 during 1 hour after the start of the ion etching.

Figure 5B:
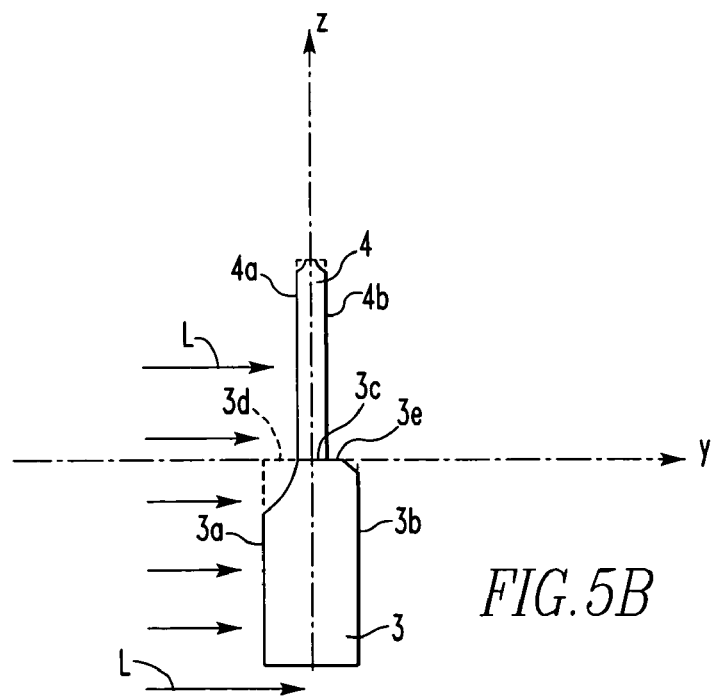

FIG. 5B shows the specimen 3 when a period of 5 minutes has passed since the start of the ion etching. As shown in this figure, the irradiated surface portions 3d and 3e irradiated with the ion beam $I_B$ have been ion-etched. Concomitantly, the left side surface 3a and right side surface 3b of the specimen 3 have been partially etched.

On the other hand, the unirradiated surface portion 3c that is covered with the shielding material 4 and thus is not irradiated with the ion beam $I_B$ remains unetched. Since the ion beam hits the specimen 3 obliquely from leftward above the shielding material 4, the left side surface 3a of the specimen 3 is more etched than the right side surface 3b. Also, the left side surface 3a is inwardly (along the z-axis) etched more than the right side surface 3b.

When the ion beam 3 hits the specimen from leftward above the shielding material 4 as described above, the gun control means 12 sends the tilt signal $\theta_1$ to the driver source 14 to tilt the ion gun 5 to the right (y-direction) at an angle of $\theta_1$ (1.5°). The driver source 14 tilts the gun-tilting mechanism 6 in response to the tilt signal $\theta_1$. As a result, the ion gun 5 tilts to the right relative to the z-axis by 1.5°.

Figure 7A:
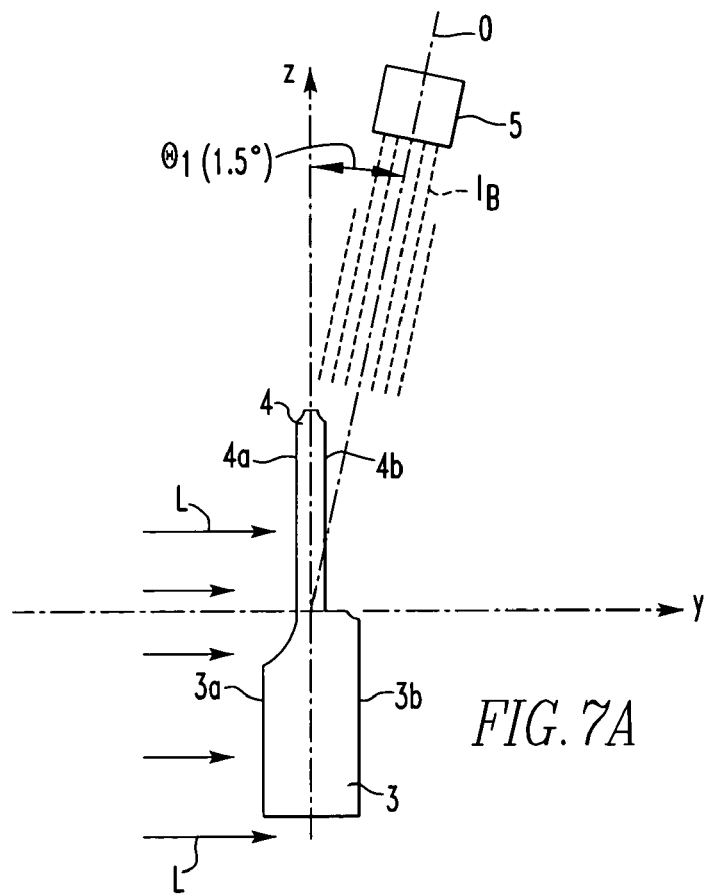
FIGS. 7A and 7B illustrate the operation of the apparatus shown in FIG. 3A.

Because of the tilt of the ion gun 5, the ion beam $I_B$ tilted to the right relative to the z-axis by $\theta_1$ (1.5°) hits the shielding material 4 and the specimen 3 obliquely from rightward above the shielding material 4 as shown in FIG. 7A. The ion-beam irradiation is performed for a given time (e.g., 5 minutes).

Figure 7B:
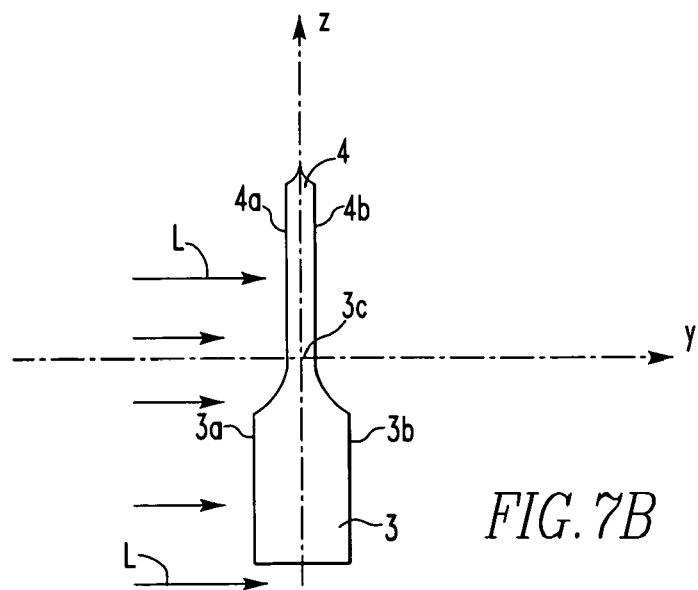

FIG. 7B shows the state of the specimen 3 after the ion gun 5 is tilted to the right and the specimen 3 is irradiated with the ion beam for 5 minutes. As shown in this figure, the right side surface 3b of the specimen 3 is etched to a great extent at this time. On the other hand, the unirradiated surface portion 3c that is covered with the shielding material 4 and has not been irradiated with the ion beam $I_B$ remains unetched.

Figure 8A:
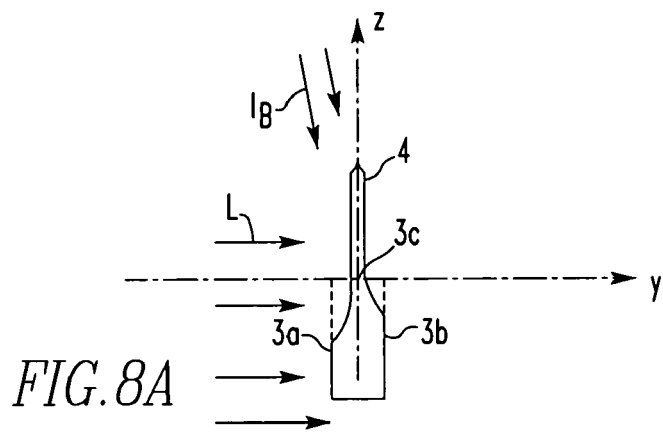
FIGS. 8A, 8B, 8C, and 8D illustrate the operation of the apparatus shown in FIG. 3A.
Figure 8B:
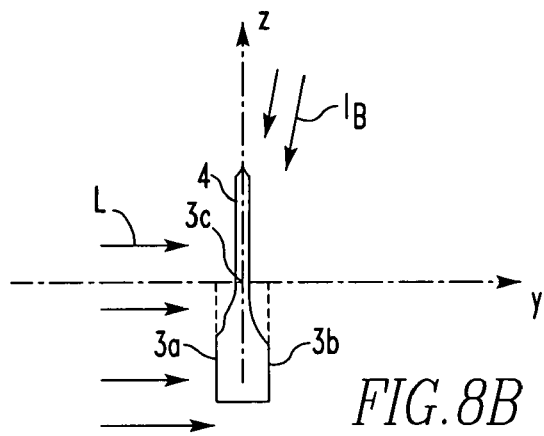
Figure 8C:
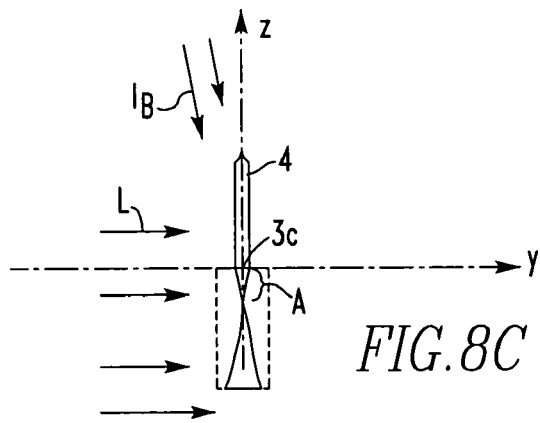

Subsequently, the ion gun 5 is tilted left and right repeatedly in the same way as in the above-described process. The specimen 3 is etched by the ion beam $I_B$ which is tilted by 1.5° left and right relative to the z-axis. FIGS. 8A to 8D show the manner in which the specimen 3 is being etched. After the state shown in FIG. 7B, the specimen 3 is etched as shown in FIG. 8A. Then, the specimen 3 is etched as shown in FIG. 8B. Thereafter, the ion gun 5 is tilted left and right plural times to ion-etch the specimen 3. As a result, the specimen 3 is etched as shown in FIG. 8C. The unirradiated surface portion 3c of the specimen 3 remains unetched as shown from FIG. 8A to FIG. 8C. On the other hand, the specimen portions which are located around the unirradiated surface portion $3c$ are gradually etched. The portion A of the specimen 3 becomes gradually thinner in going downward (-z-direction) from the unirradiated surface portion $3c$ as shown in FIG. 8C. However, a through-hole is not yet formed in the specimen 3 even at this instant of time. In the process step (5), the high-brightness pixel extraction means 10 does not yet detect the high-brightness pixels P.

Figure 8D:
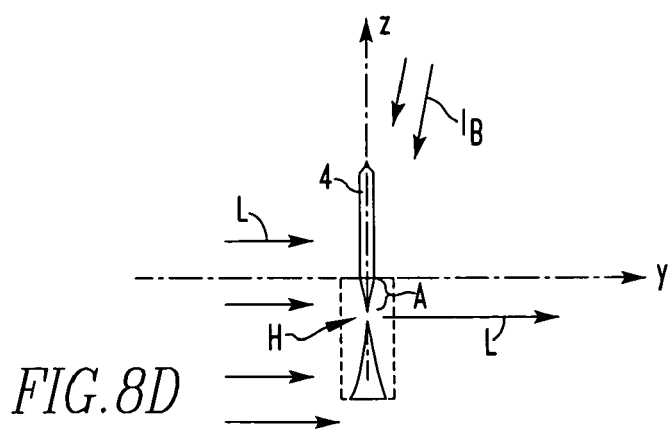

FIG. 8D shows the state in which the sense of the ion gun 5 has been varied after the state shown in FIG. 8C and the specimen 3 is still being irradiated with the ion beam $I_B$. Since the portion A of the specimen 3 shown in FIG. 8C has been further ion-etched, a through-hole H begins to be formed in the specimen 3 at instant $T_1$ as shown in FIG. 8D. The position of the through-hole H is at about 300 μm from the top surface of the specimen 3.

FIG. 9A shows the specimen image $I_{T1}$ accepted by the high-brightness pixel extraction means 10 from the imaging device 8 at instant $T_1$. As shown in this figure, only the pixel $p_{25}$ out of the pixels within the decision region D' is shining brightly. This pixel $p_{25}$ represents the light L passed through the through-hole H (see FIG. 8D). If the through-hole H becomes larger, pixels around the pixel $p_{25}$ also become bright but only the pixel $p_{25}$ is shining brightly at the instant $T_1$.

The high-brightness pixel extraction means 10 performs the process steps (1)-(5) above regarding the specimen image $I_{T1}$. In this case, in the process step (1), the extraction means 10 extracts the pixel $p_{25}$ as one of pixels having intensities greater than the threshold value K. Therefore, the extraction means 10 detects the pixel $p_{25}$ as a high-brightness pixel P contained in the decision region D' in the process step (5). The extraction means 10 sends a high-brightness pixel position signal $p_{25}$ (x, y) indicative of the position of the high-brightness pixel $p_{25}$ to the decision means 11.

The decision means 11 makes a decision according to the high-brightness pixel position signal sent in from the high-brightness pixel extraction means 10 as to whether the high-brightness pixels P extracted by the extraction means 10 form a continuous sequence of more than a given number (n) of pixels on the specimen image $I_{T1}$. It is now assumed that the number n is set to 2. The number 2 has been previously entered and set by the operator from the input means 15.

In this case, the high-brightness pixel P extracted by the extraction means 10 is only the pixel $p_{25}$. The high-brightness pixel position signal sent to the decision means 11 from the extraction means 10 is only $p_{25}$(x, y). Therefore, the decision means 11 determines that "the high-brightness pixels P extracted by the extraction means 10 does not contain any continuous sequence of more than 2 pixels on the specimen image $I_{T1}$". The decision means 11 sends an ion-beam irradiation stop signal to the gun control means 12 only when the decision made by the decision means 11 is that there is a continuous sequence of more than 2 pixels P. Therefore, in this case, the ion-beam irradiation stop signal is not sent to the gun control means 12. Consequently, the specimen 3 is continued to be irradiated with the ion beam.

FIG. 9B shows the specimen image $I_{T2}$ accepted into the high-brightness pixel extraction means 10 next to the specimen image $I_{T1}$. That is, the specimen image In accepted at the instant $T_2$ after a lapse of 2 seconds from the instant $T_1$ is shown. It can be seen by comparison of FIG. 9A and FIG. 9B that the pixel $p_{26}$ located immediately right to the pixel $p_{25}$ has come to shine brightly during the period of 2 seconds, for the following reason. The specimen 3 is further ion-etched and the through-hole H becomes slightly larger than the size shown in FIG. 8D. The pixel $p_{26}$ represents the light L passed through the through-hole H.

The high-brightness pixel extraction means 10 performs the process steps (1)-(5) regarding the specimen image $I_{T2}$. In this case, the extraction means 10 extracts pixels having intensities greater than the threshold value K in the process step (1), the pixels including pixels $p_{25}$ and $p_{26}$. Therefore, the extraction means 10 detects the pixels $p_{25}$ and $p_{26}$ as high-brightness pixels P contained in the decision region D' in the process step (5). The extraction means 10 sends high-brightness pixel position signals $p_{25}$ (x, y) and $p_{26}$ (x, y) indicative of the positions of the high-brightness pixels $p_{25}$ and $p_{26}$ to the decision means 11.

Based on the high-brightness pixel position signals $p_{25}$ (x, y) and $p_{26}$ (x, y), the decision means 11 determines that the high-brightness pixels $p_{25}$ and $p_{26}$ are laterally immediately adjacent to each other on the specimen image $I_{T2}$. As a result, the decision means 11 sends an ion-beam irradiation stop signal to the gun control means 12. The gun control means 12 receiving the beam irradiation stop signal sends a signal to the voltage source 13 to stop the ion-beam irradiation. In consequence, the release of the ion beam from the ion gun 5 is stopped. Furthermore, the gun control means 12 controls the tilt driver source 14 to stop the tilt of the gun-tilting mechanism 6.

As a result, the thin-film specimen 3 according to the present invention as shown in FIG. 9C is completed. The portion k around the through-hole H is a thin film having a thickness of about 100 Å. This thickness is adapted for TEM observation.

The case where the through-hole H is formed in the specimen 3 and a thin-film specimen is prepared with the apparatus according to the invention as shown in FIG. 3A has been described so far. As described previously, in the present invention, high-brightness pixels P appearing as the specimen is thinned are extracted. When the pixels P form a continuous sequence of more than the given number n of pixels, the ion-beam irradiation is stopped. The value of n can be set arbitrarily from the input means 15. The ion-beam irradiation can be stopped always when a thin film having a thickness adapted for TEM observation is completed, by setting the value of n to a previously empirically found optimum value.

In the case of the present invention, if the high-brightness pixels P appearing are plural in number, the ion-beam irradiation is not stopped unless they form a continuous sequence of pixels whose number exceeds the given number n. If two high-brightness pixels P appear discretely, for example, the ion-beam irradiation is not stopped. This phenomenon takes place in a case where the light L reflected after striking the specimen chamber wall is temporarily detected by the imaging device 8. On the other hand, where the through-hole H is formed in the specimen 3, the extracted high-brightness pixels P form a continuous sequence of pixels. According to the present invention where the ion-beam irradiation is stopped by detecting a sequence of high-brightness pixels P, the ion-beam irradiation is prevented from being erroneously stopped if the light L reflected after striking the specimen chamber wall is temporarily detected by the imaging device 8. The ion-beam irradiation is normally stopped only when the given through-hole H is formed in the specimen 3. Accordingly, in the present invention, a thin-film specimen adapted for TEM observation can be prepared reliably.

In the above-described embodiment, two (n=2) high-brightness pixels P form a lateral sequence of pixels (see FIG. 9B). Also, in a case where two high-brightness pixels P form a vertical or oblique sequence of pixels, the decision means 11 operates to send the ion-beam irradiation stop signal to the gun control means 12.

A case where a specimen cut out from a silicon wafer is shaped into a thin film and a section of the specimen is prepared using the apparatus of FIG. 3A is next described.

Figure 10A:
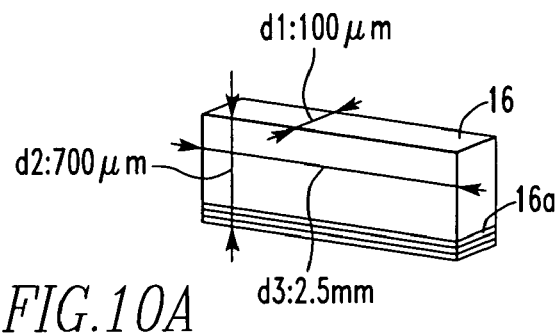
FIGS. 10A, 10B, 10C, and 10D illustrate the operation of the apparatus shown in FIG. 3A.
Figure 10B:
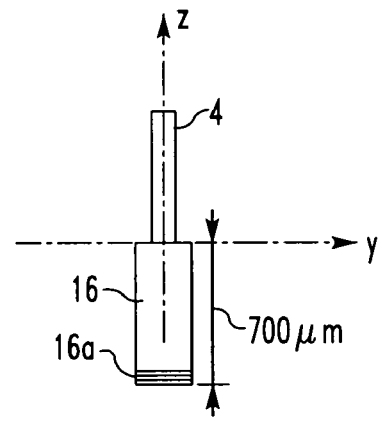

In this case, a specimen 16 having dimensions of 100 μm ($d_1$)×700 μm ($d_2$)×2.5 mm ($d_3$) as shown in FIG. 10A is first prepared. The specimen 16 has been cut out from a silicon wafer and roughly polished. The specimen 16 has a lower portion 16a having a multilayered structure. The purpose is to prepare a section of the specimen by thinning the multilayered structure portion 16a. The specimen 16 cut out in this way is disposed in the specimen chamber 2 instead of the specimen 3 of FIG. 3A. FIG. 10B shows the specimen 16 disposed in the specimen chamber 2 and the shielding material 4. As shown in FIG. 10B, the multilayered structure portion 16a of the specimen 16 is located at a distance of about 700 μm from the shielding material 4.

Where the multilayered structure portion 16a of the specimen 16 is thinned, the operator first enters "specimen type" from the input means 15 shown in FIG. 3A. In this case, "multilayered structure specimen" is entered. If this input is made, the CCU 9 sets the operation mode of the high-brightness pixel extraction means 10, decision means 11, and gun control means 12 to a "multilayered structure portion-thinning mode" corresponding to the "multilayered structure specimen". In this thinning mode, the multilayered structure portion 16a of the specimen 16 is thinned.

When the operator enters "start of etching" from the input means 15, the gun control means 12 of the CCU 9 operates in the "multilayered structure portion-thinning mode". That is, the gun control means 12 sends a tilt signal $\theta_1$ to the tilt driver source 14 to tilt the ion gun 5 to the left (-y-direction) at an angle of $\theta_1$ (e.g., 0.7°). The driver source 14 tilts the gun-tilting mechanism 6 in response to the tilt signal $\theta_1$. As a result, the ion gun 5 tilts to the left relative to the z-axis by 0.7°. The value of the tilt angle $\theta_1$ (0.7°) has been entered and set by the operator from the input means 15.

When the "start of etching" is entered, the gun control means 12 of the CCU 9 sends a signal to the voltage source 13 to release the ion beam $I_B$ from the ion gun 5. The voltage source 13 applies a given voltage between the electrodes of the gun 5 to release the beam $I_B$. As a result, the beam $I_B$ is emitted from the gun 5 tilted at an angle of $\theta_1$ (0.7°) to the left relative to the z-axis.

Figure 10C:
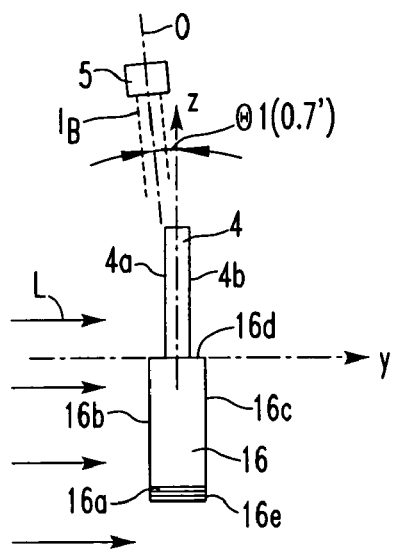

When "start of etching" is entered, the CCU 9 turns on the power supply of the light source 7. Light L is emitted from the light source 7. The light L hits the left side surface 16b of the specimen 16 and the left side surface 4a of the shielding material 4 as shown in FIG. 10C. The ion beam $I_B$ released from the ion gun 5 and tilted at an angle of $\theta_1$ (0.7°) to the left relative to the z-axis hits the shielding material 4 and specimen 16 obliquely from leftward above the shielding material 4 as shown in FIG. 10C. The ion-beam irradiation is continued for a given time (e.g., 5 minutes).

When the "start of etching" is entered, the CCU 9 sends a signal to the imaging device 8 to operate it. The imaging device 8 starts to continuously image the surface of the specimen facing away from the illuminated surface, i.e., the right side surface 16c of the specimen 16. The specimen image (contained within the region C of FIG. 4) taken by the imaging device 8 is sent to the high-brightness pixel extraction means 10.

Figure 11A:
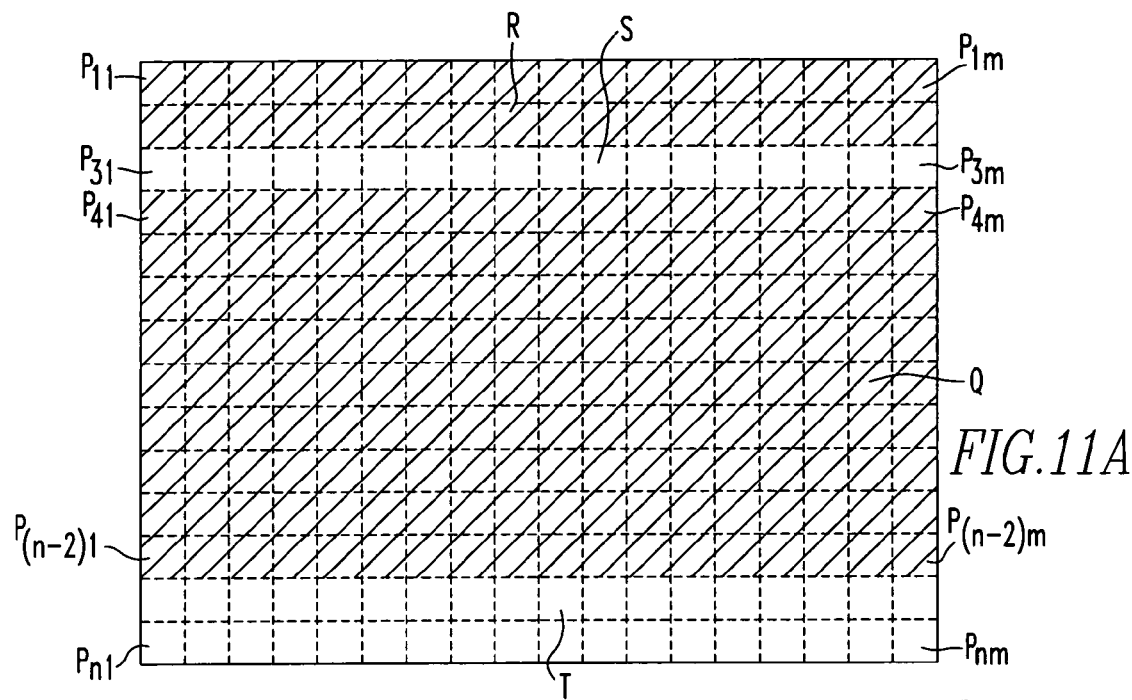
FIGS. 11A, 11B, and 11C illustrate the operation of the apparatus shown in FIG. 3A.

The high-brightness pixel extraction means 10 accepts the specimen images taken by the imaging device 8 at given intervals of time (e.g., at intervals of 2 seconds). First, the extraction means 10 accepts the first taken image of the specimen, i.e., the specimen image $I_1$ taken at the beginning of etching. The image $I_1$ taken in is shown in FIG. 11A. The dotted line indicates the boundary between adjacent pixels. In FIG. 11A, an image Q represents the right side surface 16c of the specimen 16. The image Q is made up of pixels $p_{41}$, $p_{42}, \ldots, p_{4m}, \ldots, p_{(n-2)1}, \ldots, p_{(n-2)m}$. The specimen 16 does not transmit the light L emitted from the light source 7. The right side surface 16c of the specimen 16 is not illuminated with the light and so the image Q is totally dark.

In FIG. 11A, an image R represents the lower end (right side surface 4b) of the shielding material 4. The image R is made up of pixels $p_{11}, p_{12}, \ldots, p_{1m}, p_{21}, \ldots, p_{2m}$. The image R is totally dark in the same way as the image Q.

In FIG. 11A, an image S represents the light L passed through the gap between the shielding material 4 and specimen 16. The image S is made up of pixels $p_{31}, \ldots, p_{3m}$. The image S is bright in conformity with the brightness of the light L.

In FIG. 11A, an image T represents the light L passed under the specimen 16. The image T is made up of pixels $p_{(n-1)1}, \ldots, p_{(n-1)m}, \ldots, p_{nm}$. The image T is bright in conformity with the brightness of the light L, in the same way as the image S.

(6) The high-brightness pixel extraction means 10 compares the signal intensities derived from the pixels ($p_{11}$ to $p_{nm}$) making up the accepted specimen image $I_1$ produced at the beginning of etching with a threshold value K, and extracts pixels having intensities greater than the threshold value K. The threshold value K has been previously set by the operator from the input means 15 such that pixels ($p_{31}, \ldots, p_{3m}$ and $p_{(n-1)1}, \ldots, p_{(n-1)m}, \ldots, p_{nm}$ at the present instant of time) representing the light L are extracted. That is, as shown in FIG. 6B, the threshold value K is set to a value slightly lower than the intensity J of the pixels representing the light L. At the present instant, the intensities of pixels $p_{41}, p_{42}, \ldots, p_{4m}, \ldots, p_{(n-2)1}, \ldots, p_{(n-2)m}$ making up the image Q of the right side surface of the specimen and the intensities of pixels $p_{13}, p_{12}, \ldots, p_{1m}, p_{21}, \ldots, p_{2m}$ making up the image R of the shielding material are the intensity L in FIG. 6B. The intensity L is almost zero.

(7) Since the threshold value K is set as described above, the high-brightness pixel extraction means 10 extracts pixels $p_{31}, \ldots, p_{3m}$ and $p_{(n-1)1}, \ldots, p_{(n-1)m}, \ldots, p_{nm}$ representing the light L. The extraction means 10 extracts the pixels representing the light L in this way, thus identifying pixels corresponding to the upper end 16d (FIG. 10C) and lower end 16e (FIG. 10C), respectively, of the specimen 16. That is, the extraction means 10 identifies pixels $p_{41}, p_{42}, \ldots, p_{4m}$ as pixels corresponding to the upper end 16d of the specimen, based on the extracted pixels $p_{31}, \ldots, p_{3m}$. Similarly, the extraction means 10 identifies pixels $p_{(n-2)1}, \ldots, p_{(n-2)m}$ as pixels corresponding to the lower end 16e of the specimen, based on the extracted pixels $p_{(n-1)1}, \ldots, p_{(n-1)m}$.

(8) After identifying the pixels $p_{41}, p_{42}, \ldots, p_{4m}$ corresponding to the upper end 16d of the specimen and the pixels $p_{(n-2)1}, \ldots, p_{(n-2)m}$ corresponding to the lower end 16e of the specimen in this way, the high-brightness pixel extraction means 10 stores information U about the positional relation between the pixels $p_{(n-2)1}, \ldots, p_{(n-2)m}$ and the pixels $p_{41}, p_{42}, \ldots, p_{4m}$. That is, the extraction means 10 stores the information U about the distance (indicated by the number of pixels) of the pixel $p_{(n-2)1}$ from the pixel $p_{41}$ and the distance (indicated by the number of pixels) of the pixel $p_{(n-2)2}$ from the pixel $p_{42}$.

The processing (the above-described process steps (6)-(8)) performed by the extraction means 10 regarding the specimen image $I_1$ has been described so far. When a period of 2 seconds elapses since acceptance of the specimen image $I_1$ the extraction means 10 accepts the specimen image $I_2$ taken by the imaging device 8. The extraction means 10 performs the above-described process step (6) regarding the specimen image $I_2$. After the execution of the process step (6), the next process steps (9) and (10) are performed.

(9) In response to the setting of the threshold value K, the extraction means 10 extracts pixels $p_{31}, \ldots, p_{3m}$ and $p_{(n-1)1}, \ldots, p_{(n-1)m}, \ldots, p_{nm}$ representing the light L. The extraction means 10 identifies pixels $p_{41}, p_{42}, \ldots, p_{4m}$ as pixels corresponding to the upper end 16d of the specimen, based on the extracted pixels $p_{31}, \ldots, p_{3m}$. The extraction means 10 identifies the pixels $p_{(n-2)1}, \ldots, p_{(n-2)m}$ (see FIG. 11A) as the pixels corresponding to the lower end 16e of the specimen, based on the information about the identified pixels $p_{41}, p_{42}, \ldots, p_{4m}$ and on the information U found in the process step (8).

(10) The extraction means 10 refers to the results of the extraction performed in the process step (6) and makes a decision as to whether the pixels $p_{(n-2)1}, \ldots, p_{(n-2)m}$ (corresponding to the lower end 16e of the specimen) identified in the process step (9) contain high-intensity pixels P having intensities greater than the threshold value K.

The contents of the process step (10) have been described so far. At this instant of time, the lower end 16e of the specimen is hardly etched. The accepted specimen image 12 is similar to the specimen image $I_1$ taken 2 seconds earlier. Therefore, the extraction means 10 determines that no high-brightness pixels P are contained in the pixels $p_{(n-2)1}, \ldots, p_{(n-2)m}$ corresponding to the lower end 16e of the specimen in response to the specimen image $I_2$. Consequently, the extraction means 10 produces no output signal to the decision means 11.

Then, the extraction means 10 accepts specimen images $I_3$, $I_4, \ldots$ at intervals of 2 seconds, and performs the process steps (6), (9), and (10) regarding the specimen images. In practice, the lower end 16e of the specimen is not thinned unless a period of at least 1 hour elapses since the start of ion etching. Therefore, the extraction means 10 produces no output signal to the decision means 11 during a period of 1 hour from the start of the ion etching. Subsequently, the ion gun 5 is repeatedly tilted left and right in the same way as for the aforementioned bulk specimen. The specimen 16 is etched by the ion beam $I_B$ that is tilted at an angle of 0.7° left and right relative to the z-axis.

Figure 10D:
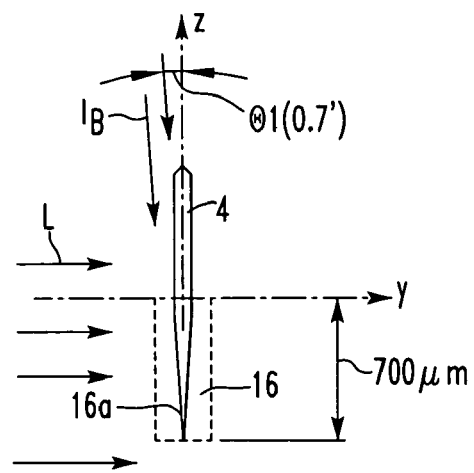
Figure 11B:
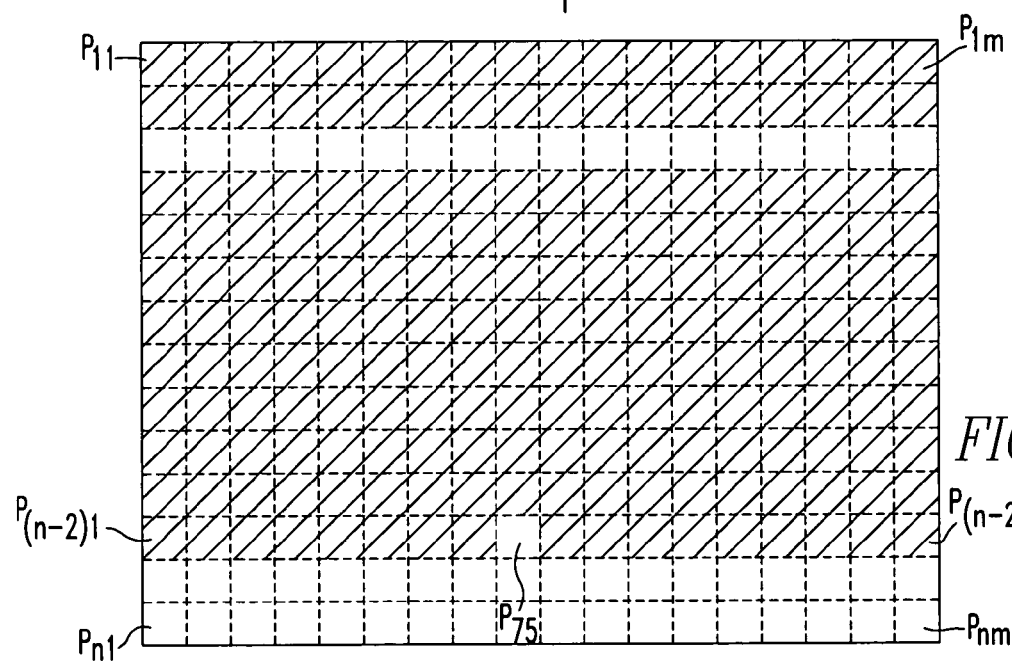

FIG. 10D shows the state occurring at instant $T_1$ in which the specimen 16 has been ion-etched considerably and the lower end 16a of the specimen has been thinned considerably. FIG. 11B shows the specimen image $I_{T1}$ accepted by the high-brightness pixel extraction means 10 from the imaging device 8 at the instant $T_1$.

Figure 11C:

As shown in FIG. 11B, only the pixel $p_{75}$ is shining brightly out of the pixels $p_{(n-2)1}, \ldots, p_{(n-2)m}$ corresponding to the lower end 16e of the specimen. The pixel $p_{75}$ represents the light L and is a high-brightness pixel appearing with thinning of the lower end 16a of the specimen. That is, as the lower end 16a of the specimen is thinned, a part of the lower end 16a is cut away as shown in FIG. 11C, resulting in a cutout 16f. The light L passed through the cutout 16f is detected by the imaging device 8. Consequently, the high-brightness pixel $p_{75}$ appears on the specimen image $I_{T1}$.

The high-brightness pixel extraction means 10 performs the process steps (6), (9), and (10) regarding the specimen image $I_{T1}$. In this case, in the process step (6), the extraction means 10 extracts the pixel $p_{75}$ as one of pixels having intensities greater than the threshold value K. In the process step (10), the extraction means 10 detects the pixel $p_{75}$ as a high-brightness pixel P. The extraction means 10 sends a high-brightness pixel position signal $p_{75}$ (x, y) indicative of the position of the high-brightness pixel $p_{75}$ to the decision means 11.

The decision means 11 makes a decision based on the high-brightness pixel position signal sent in from the high-brightness pixel extraction means 10 as to whether the high-brightness pixels P extracted by the extraction means 10 form a continuous sequence of more than a given number (n) of pixels on the specimen image $I_{T1}$. The number n is set to 2 in this example. The number 2 has been previously entered and set by the operator from the input means 15.

In this case, the high-brightness pixel P extracted by the extraction means 10 is only the pixel $p_{75}$. The high-brightness pixel position signal sent to the decision means 11 from the decision means 10 is only $p_{75}$ (x, y). Therefore, the decision means 11 determines that "the high-brightness pixels P extracted by the extraction means 10 does not form a continuous sequence of two or more pixels on the specimen image $I_{T1}$". The decision means 11 sends an ion-beam irradiation stop signal to the gun control means 12 only when the decision means 11 has determined that "the high-brightness pixels P form a continuous sequence of two or more pixels". Therefore, in this case, the ion-beam irradiation stop signal is not sent to the gun control means 12. Consequently, the ion-beam irradiation of the specimen 3 is continued.

Figure 12A:
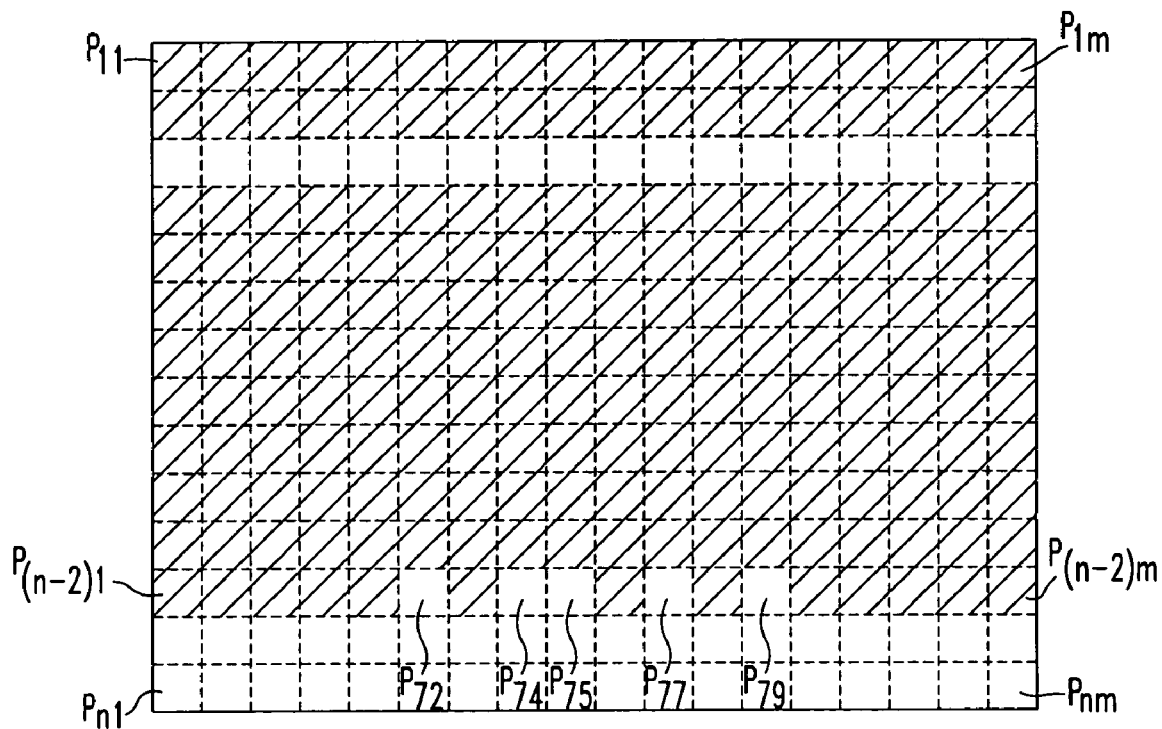
FIGS. 12A and 12B illustrate the operation of the apparatus shown in FIG. 3A.
Figure 12B:
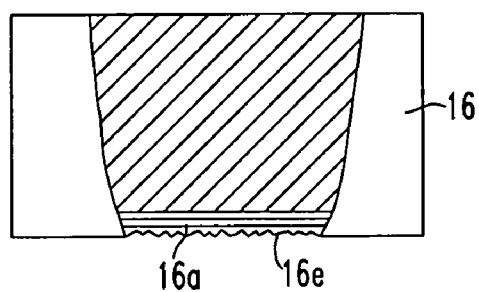

FIG. 12A shows the specimen image $I_{T2}$ accepted into the high-brightness pixel extraction means 10 next to the specimen image $I_{T1}$. That is, the specimen image $I_{T2}$ accepted at the instant $T_2$ after a lapse of 2 seconds from the instant $T_1$ is shown. As can be seen by comparing FIG. 12A and FIG. 11B, pixels $p_{72}, p_{74}, p_{77},$ and $p_{79}$ have come to shine brightly during the period of 2 seconds, for the following reason. The lower end 16a of the specimen is thinned further by the ion etching and becomes sawtoothed as shown in FIG. 12B. The pixels $p_{72}, p_{74}, p_{75}, p_{77},$ and $p_{79}$ represent the light L passed through the gaps between the teeth of the sawtoothed portion.

The high-brightness pixel extraction means 10 performs the process steps (6), (9), and (10) regarding the specimen image $I_{T2}$. In this case, during the process step (6), the extraction means 10 extracts pixels including $p_{72}, p_{74}, p_{75}, p_{77},$ and $p_{79}$ as pixels having intensities greater than the threshold value K. Therefore, during the process step (10), the extraction means 10 detects the pixels $p_{72}, p_{74}, p_{75}, p_{77},$ and $p_{79}$ as high-brightness pixels P. The extraction means 10 sends high-brightness pixel position signals $p_{72}$ (x, y), $p_{74}$ (x, y), $p_{75}$ (x, y), $p_{77}$ (x, y), and $p_{79}$ (x, y) indicative of the positions of the high-brightness pixels $p_{72}, p_{74}, p_{75}, p_{77},$ and $p_{79}$ to the decision means 11.

The decision means 11 determines, based on the high-brightness pixel position signals, that the high-brightness pixels $p_{74}$ and $p_{75}$ form a continuous sequence of two pixels in the edge direction of the lower end of the specimen on the specimen image $I_{T2}$. As a result, the decision means 11 sends an ion-beam irradiation stop signal to the gun control means 12. The gun control means 12 receiving the stop signal sends a signal to the voltage source 13 to stop the ion-beam irradiation. In consequence, the emission of the ion beam from the ion gun 5 is stopped. Furthermore, the gun control means 12 controls the tilting driver source 14 to stop the tilting of the gun-tilting mechanism 6.

As a result, a thin-film specimen 16 (FIG. 12B) according to the present invention is completed. The multilayered structure portion 16a is thinnest, and the thickness is about 100 Å, which is adapted for TEM observation.

While the operation of the apparatus shown in FIG. 3A has been described so far, the present invention is not limited to the above-described embodiment but rather embraces other modified embodiments.

For example, in the above embodiment, the decision means 11 supplies the ion-beam irradiation stop signal to the gun control means 12 if the high-brightness pixels P are judged to form a continuous sequence of more than a given number of pixels on the specimen image. Instead of the stop signal, the decision means 11 may supply a finishing signal to the gun control means 12. The gun control means 12 receiving the finishing signal sends a signal to the voltage source 13 to reduce the intensity of the ion beam hitting the specimen. Consequently, the voltage applied to the extraction voltage of the ion gun 5 is set lower than heretofore. This reduces the amount of ions released from the ion gun 5. The intensity of the ion beam is set lower than heretofore in this way, and the specimen is finished. This finishing process is performed, for example, for 30 minutes. Then, the ion beam-irradiation of the specimen is stopped.

Furthermore, in the above-described embodiment, the high-brightness pixel extraction means 10 takes in images from the imaging device 8 at intervals of 2 seconds. Images may be continuously taken in from the imaging device 8 and the images may then be processed in the manner as described above.

In addition, in the above embodiment, the ion gun 5 is tilted left and right. Alternatively, two ion guns may be disposed. The ion beam emitted from one gun may be directed at the shielding material and at the specimen obliquely from leftward above the shielding material. The ion beam produced from the other gun may be directed at the shielding material and at the specimen obliquely from rightward above the shielding material. In this scheme, a thin-film specimen can be prepared at a velocity that is about twice the velocity achieved in the above-described embodiment.

Further, in the above embodiment, the ion beam is directed at the left and right side surfaces of the specimen. Alternatively, the ion beam may be directed at only one of the side surfaces, and the specimen may be thinned.

Yet further, in the above embodiment, the ion gun 5 is tilted left and right relative to the z-axis. Alternatively, the ion gun may be fixed without being tilted. The specimen and shielding material may be tilted together.

Still further, in the above embodiment, the specimen is etched with the ion beam that is tilted left and right relative to the z-axis. Alternatively, the process step consisting of etching the specimen with the ion beam passing along the z-axis to irradiate the specimen with the ion beam from just above the shielding material and the process step consisting of etching the specimen with the ion beam tilted to one side (left or right) relative to the z-axis, for example, at an angle of 3° may be alternately and repeatedly performed.

Having thus described our invention with the detail and particularity required by the Patent Laws, what is desired protected by Letters Patent is set forth in the following claims.

The invention claimed is:

1. A method for preparing a thinned specimen by irradiating at least one of the side surfaces of the specimen with an ion beam to ion-etch the specimen, said method comprising the steps of:
(a) directing the ion beam at the specimen, directing light at one side surface of the specimen, and imaging the other side surface of the specimen with an imaging device;
(b) extracting high-brightness pixels which form the specimen image and which have intensities becoming greater than a given threshold value as the specimen is thinned;
(c) making a decision as to whether the extracted high-brightness pixels form a continuous sequence of pixels whose number is in excess of a given number on the specimen image; and
(d) stopping the ion-beam irradiation of the specimen or varying conditions under which the specimen is irradiated with the ion beam if the decision at the step (c) is affirmative (YES).

2. A method of specimen preparation as set forth in claim 1, further comprising the step of placing a belt-like, ribbon-like, or tape-like shielding material so as to stand substantially uprightly over the specimen to form an unirradiated surface portion of the specimen and irradiated surface portions of the specimen located on opposite sides of the unirradiated surface portion, and wherein
(A) the ion beam being directed at the shielding material and one side of the specimen obliquely from above the shielding material or from immediately above the shielding material,
(B) the ion beam being directed at the shielding material and the other side of the specimen obliquely from above the shielding material, and
(C) the irradiated surface portions being ion-etched while leaving the unirradiated surface portion unetched to ion-etch the side surfaces of the specimen, whereby preparing a thin-film specimen that becomes thinner in going downward from the unirradiated surface portion.

3. A method of specimen preparation as set forth in claim 2, wherein where a direction in which the ion beam is directed is set such that a through-hole is formed in the specimen, a decision is made as to whether said high-brightness pixels form a continuous vertical, lateral, or oblique sequence of pixels whose number is in excess of a given number on the specimen image.

4. A method of specimen preparation as set forth in claim 2, wherein where a direction in which the ion beam is directed is set such that a lower end of the specimen is thinned, a decision is made as to whether said high-brightness pixels are present in positions corresponding to the lower end of the specimen on the specimen image and form a continuous sequence of pixels whose number is in excess of a given number in an edge direction of the lower end of the specimen.

5. A method of specimen preparation as set forth in claim 1, wherein where said decision at the step (c) is affirmative (YES), the ion beam hitting the specimen is weakened and a finishing process is performed.

6. A specimen preparation apparatus for preparing a thinned specimen by irradiating at least one of left and right side surfaces of the specimen with an ion beam to ion-etch the specimen, said specimen preparation apparatus comprising:
light illumination means for directing light at any one side surface of the specimen;
imaging device for imaging the other side surface of the specimen;
high-brightness pixel extraction means for extracting high-brightness pixels which form the specimen image imaged by the imaging device and which have intensities becoming greater than a given threshold value as the specimen is thinned;
decision means for making a decision as to whether the extracted high-brightness pixels form a continuous sequence of pixels whose number is in excess of a given number on the specimen image; and
means which, when said decision is affirmative (YES), stops the ion-beam irradiation of the specimen or varies conditions under which the specimen is irradiated with the ion beam.

7. A specimen preparation apparatus as set forth in claim 6, further comprising:
- a belt-like, ribbon-like, or tape-like shielding material placed to stand substantially uprightly over the specimen to form an unirradiated surface portion of the specimen and irradiated surface portions of the specimen located on opposite sides of the unirradiated surface portion;
- means for directing the ion beam at one side surface of the shielding material and at the specimen obliquely from above the shielding material; and
- means for directing the ion beam at the other side surface of the shielding material and at the specimen obliquely from above the shielding material;
- wherein a direction in which the ion beam is directed is so set as to prepare the thin-film specimen that becomes thinner in going downward from the unirradiated surface portion.

8. A specimen preparation apparatus as set forth in claim 7, wherein where the direction in which the ion beam is directed is so set that a through-hole is formed in the specimen, said decision means makes a decision as to whether said high-brightness pixels form a continuous vertical, lateral, or oblique sequence of pixels whose number is in excess of a given number on the specimen image.

9. A specimen preparation apparatus as set forth in claim 7, wherein where the direction in which the ion beam is directed is so set that the lower end of the specimen is thinned, said high-brightness pixel extraction means extracts said high-brightness pixels appearing in positions corresponding to the lower end of the specimen on the specimen, and said decision means makes a decision as to whether the extracted pixels form a continuous sequence of pixels whose number is in excess of a given number on the specimen image.

\* \* \* \* \*